United States Patent [19]

Aono et al.

[11] Patent Number: 4,904,690
[45] Date of Patent: Feb. 27, 1990

[54] CHROMONE DERIVATIVES USEFUL AS ANTITUMOR AGENTS

[75] Inventors: Tetsuya Aono, Nagaokakyo; Katsutoshi Mizuno, Toyonaka, both of Japan

[73] Assignee: Takeda Chemical Industries, Ltd., Osaka, Japan

[21] Appl. No.: 162,765

[22] Filed: Mar. 1, 1988

[30] Foreign Application Priority Data

Mar. 2, 1987 [JP] Japan .................. 62-49523

[51] Int. Cl.⁴ .................. A61K 31/35; C07D 311/30
[52] U.S. Cl. .................. 514/456; 549/401
[58] Field of Search .................. 549/401; 514/456

[56] References Cited

U.S. PATENT DOCUMENTS 4,602,034  7/1986  Briet et al. .................. 549/401

FOREIGN PATENT DOCUMENTS 0080934  6/1983  European Pat. Off. .

OTHER PUBLICATIONS

Atassi et al., Chemical Abstracts, vol. 104 (1986), No. 15, p. 19, Abstract No. 12257b.

Zaharka et al., Chemical Abstracts, vol. 106 (1987), No. 3, p. 37, Abstract No. 12501j.

Atassi et al., Eur. J. Med. Chem.—Chim. Ther. 1985—20, No. 5, pp. 393–402.

O'Dwyer et al., Cancer Chemother. Pharmacol. (1987) 19, pp. 6–10.

*Primary Examiner*—Nicky Chan
*Attorney, Agent, or Firm*—Wenderoth, Lind & Ponack

[57] ABSTRACT

A novel chromone derivative having a strong antitumor activity of the general formula:

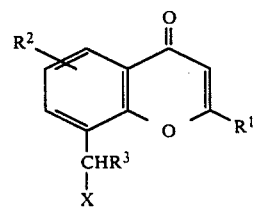

wherein $R^1$ is an unsaturated alkyl or cycloalkyl group having 3 to 7 carbon atoms; $R^2$ is hydrogen atom or a halogen atom; $R^3$ is hydrogen atom or a lower alkyl group; and X is carboxyl group, or its salt, ester or amide.

5 Claims, No Drawings

CHROMONE DERIVATIVES USEFUL AS ANTITUMOR AGENTS

FIELD OF THE INVENTION

The present invention relates to novel chromone derivatives having antitumor activity.

BACKGROUND OF THE INVENTION

In general, the real state of chemotherapy of cancer is such that it is difficult to obtain sufficient therapautic effect because of toxicity and side effects of medicines. Particularly, there are few medicines which are effective against solid cancer and, therefore, development of a medicine which is effective against solid cancer but has high safety is an urgent technical subject in this art.

In this respect, a flavone acetic acid of the formula II:

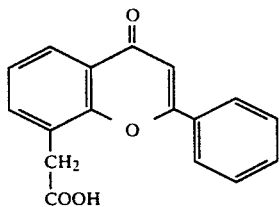

[II]

is noted as a compound effective against solid cancer such as colon 38 and the like in an animal test [Daniel S. Zaharka et al., Cancer Treatment Reports, 70, 1415 (1986); Japanese Patent Laid Open Publication No. 58-96082 (corresponding to AU-8290-728); Eur. J. Med. Chem. Chim. Ther., 1985-20, No. 5, pp393-402]. However, in order to use this compound as a medicine practically, it seems that it is necessary to further improve usefulness thereof, for example, by further enhancing its antitumor activity and making its side effect weaker.

OBJECTS AND SUMMARY OF THE INVENTION

Under these circumstances, the present inventors have synthesized various novel chromone derivatives and have studied antitumor activity of each derivative. As the results, it has been found that a novel chromone derivative of the general formula:

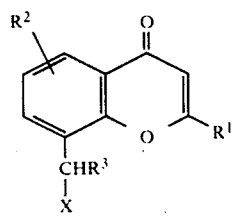

[I]

wherein $R^1$ is an unsaturated alkyl or cycloalkyl group having 3 to 7 carbon atoms; $R^2$ is hydrogen atom or a halogen atom; $R^3$ is hydrogen atom or a lower alkyl group; and X is carboxyl group or its salt, ester or amide has a strong antitumor activity.

The present invention has been completed based on this finding.

Thus, according to the present invention, there is provided the novel chromone derivative of the general formula [I] and an antitumor pharmaceutical composition comprising as an effective ingredient the novel chromone derivative.

DETAILED DESCRIPTION OF THE INVENTION

In the general formula [I], examples of the unsaturated alkyl group represented by $R^1$ include, for example, propen-1-yl, propen-2-yl, 1-buten-1-yl, 1-buten-2-yl, 1,3-butadien-1-yl, 2-penten-3-yl, 1-penten-2-yl, 2-hexen-3-yl, 1-hexen-2-yl, 3-hepten-4-yl and the like. The preferred unsaturated alkyl group is that having 3 to 5 carbon atoms. Examples of the unsaturated cycloalkyl group include, for example, cyclopenten-1-yl, cyclohexen-1-yl, 1,3-cyclohexadien-1-yl, cyclohepten-1-yl and the like. The preferred unsaturated cycloalkyl group is that having 5 to 6 carbon atoms.

Examples of the lower alkyl group represented by $R^3$ include those having 1 to 3 carbon atoms, particularly, methyl and ethyl groups. As the halogen atom represented by $R^2$, there can be exemplified, fluorine, chlorine and bromine.

It is preferable that the salt of the compound represented by the formula [I] is a pharmaceutically acceptable salt. Example of the pharmaceutically acceptable salt include salts with metals such as alkaline metals (e.g., sodium, potassium, etc.), alkaline earth metals (e.g., calcium, magnesium, etc.), aluminum and the like; ammonium salt and the like.

As the ester, there can be exemplified esters formed from the carboxylic acid of the formula [I] and alcohols having 1 to 6 carbon atoms (e.g., methanol, ethanol, propanol, isopropanol, glycerol, butanol, isobutanol, pentyl alcohol, neopentyl alcohol, 2,2-dimethyl-1,3-dioxolan-4-methanol, etc.). Among them, alcohols having 1 to 3 carbon atoms are preferable. As the amide, there can be exemplified amides formed with the carboxylic acid of the formula [I] and ammonia, lower alkyl amines having 1 to 4 carbon atoms (e.g., methylamine, dimethylamine, ethylamine, diethylamine, propylamine, etc.), cyclic amines (e.g., pyrrolidine, piperidine, morpholine, etc.), aromatic amines (aniline, N-methylaniline, etc.) and the like.

Hereinafter, the compound of the general formula [I], its salt, ester and amide are generally referred to as the compound [I].

When $R^3$ of the general formula [I] is a lower alkyl group, there are two stereoisomers of R-and S-configurations in the compound [I]. All the isolated isomers and a mixture thereof as well as the racemate thereof are included within the scope of the present invention.

The compound [I] of the present invention can be prepared, for example, by the method as shown in Scheme-I.

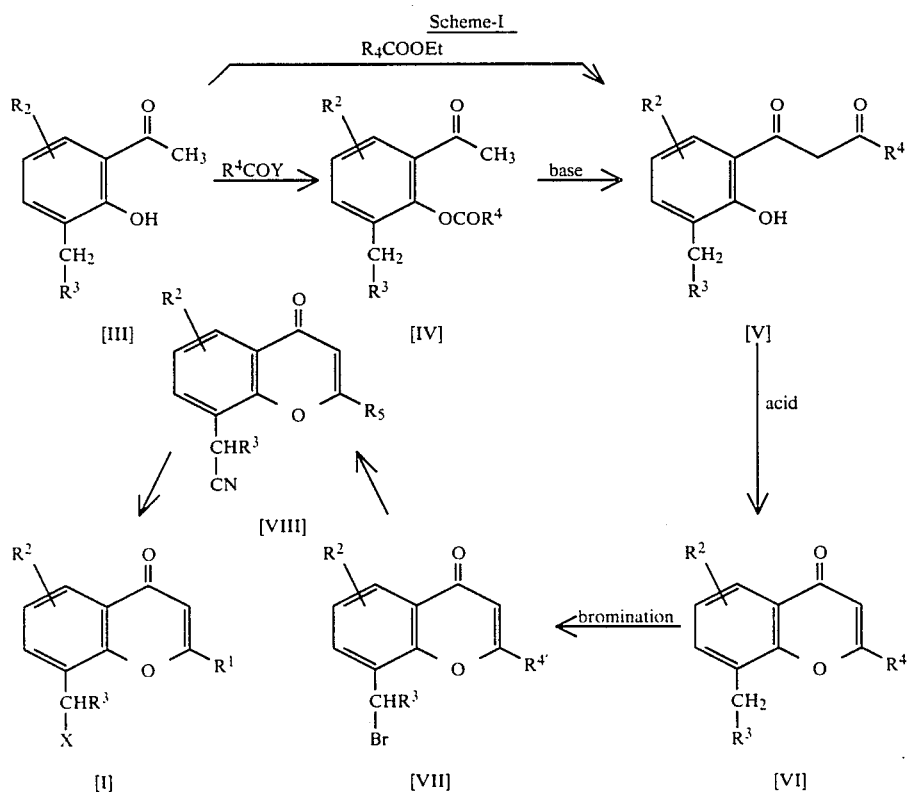

In Scheme-I, $R^1$, $R^2$, $R^3$ and X are as defined above; $R^4$ is hydrogenated $R^1$; $R^{4'}$ is $R^4$ brominated at α-position; $R^5$ has the meaning of $R^1$ or $R^{4'}$; and Y is hydroxy group or chlorine atom.

That is, the compound [V] can be obtained by reacting the compound [III] with an ester of the formula $R^4COOEt$ in the presence of a base. Alternatively, the compound [III] can be reacted with a carboxylic acid or acid chloride of the formula $R^4COY$ to obtain the ester [IV] and then subjecting it to acyl group rearrangement with a base to obtain the compound [V]. When the ester of the formula $R^4COOEt$ and the compound [III] are reacted to obtain the compound [V], for example, the ester and the compound [III] can be simply heated with stirring in toluene in the presence of a base such as sodium hydride. In order to obtain the compound [IV] by esterification of the compound [III], the compound [III] can be reacted with the carboxylic acid of the formula $R^4COY$ (Y is OH) in the presence of an acid catalyst, or can be reacted with the acid chloride of the formula $R^4COY$ (Y is Cl) in the presence of a base such as triethylamine, pyridine or the like. When the compound [IV] is subjected to acyl group rearrangement to obtain the compound [V], usually, sodium hydride, sodium hydroxide, potassium hydroxide or the like can be used as the base. In general, there can be used as a solvent pyridine, N,N-dimethylformamide or the like in this step.

The compound [III] used as the starting material and the compounds of the formulas $R^4COOEt$ and $R^4COY$ are known, or are prepared according to a known method.

When the compound [V] is cyclized to obtained the compound [VI], in general, the acid to be used for the catalyst is trifluoroacetic acid, sulfuric acid, sulfuric acid-acetic acid, hydrochloric acid or the like. As a solvent, there can be used water, acetic acid, methylene chloride or the like.

When the compound [VI] is brominated to obtain the compound [VII], for example, N-bromosuccinimide is used as the brominating agent. As a solvent, there can be used benzene, carbon tetrachloride or the like. The reaction is carried out in the presence of a small amount of azobisisobutyronitrile or benzoyl peroxide. Usually, the reaction is carried out at 50° to 80° C. In this step, not only $R^3$ is replaced by bromine but also $R^1$ is substituted with bromine to form $R^{4'}$.

When the compound [VII] is subjected to a cyanogenation reaction, the nitrile compound [VIII] is obtained.

Examples of the cyanogenation method include a method wherein dimethyl sulfoxide, N,N-dimethylformamide, ethanol or the like is used as a solvent, and sodium cyanide or potassium cyanide is used as a cyanogenating agent; a method wherein chloroform-water is used as a solvent, sodium cyanide or potassium cyanide is used as a cyanogenating agent and a quaternary ammonium salt (e.g., benzyltrimethylammonium chloride, benzyltriethylammonium chloride, tetrabutylammonium chloride, etc.) is used as a phase transfer catalyst; a method wherein a quaternary ammonium cyanide (e.g., benzyltrimethylammonium cyanide, tetrabutylammonium cyanide, etc.) is used as a cyanogenating agent; and the like.

The compound [I] can be obtained by subjecting the compound [VIII] to solvolysis and if necessary, followed by subjecting the resultant to dehydrobromination.

In general, the solvolysis of the nitrile is carried out by hydrolysis wherein water is used as a solvent, or by alcoholysis wherein an alcohol is used as a solvent. The solvolysis is generally carried out in the presence of a catalyst. As the catalyst, there can be used, for example, hydrogen halides (e.g., hydrogen chloride, hydrogen bromide, etc.); inorganic acids such as sulfuric acid, phosphoric acid, polyphosphoric acid and the like; organic acids such as formic acid, acetic acid, p-toluenesulfonic acid and the like; and Lewis acids such as boron trifluoride, titanium tetrachloride and the like. These catalysts can be used alone or in combination thereof. The reaction temperature varies depending upon a particular catalyst used. However, in general, the reaction can be carried out with cooling, at room temperature or with heating. The reaction time is not specifically limited. Since reaction conditions vary depending upon a particular product, the reaction conditions can be suitably chosen according to the desired objective compound.

For example, when an alcohol is used as the solvent, a hydrogen halide, sulfuric acid or p-toluenesulfonic acid is used as the catalyst and the reaction is carried out at an elevated temperature, there can be obtain the compound [I] wherein X is an carboxylic acid ester group. And, when water is used as the solvent, there can be obtain the compound [I] wherein X is carboxyl group. Further, when conc. sulfuric acid, conc. hydrogen halide or the like is used as the catalyst and the reaction is carried out with cooling, or when boron trifluoride is used at room temperature, there can be obtain the compound [I] in the form of an amide.

When compound [VIII] wherein $R^5$ is $R^{4'}$ is subjected to solvolysis at an elevated temperature, bromine contained in $R^5$ group is removed by dehydrobromination and $R^5$ group is changed to the unsaturated alkyl of $R^1$. When the solvolysis is carried out at a low temperature, bromine in $R^5$ group may be remained without dehydrobromination. In this case, the remaining bromide can be removed by treatment with a base to change $R^5$ containing bromine to $R^1$. As the base of this treatment, there can be used lines (e.g., triethylamine, etc.), potassium carbonate, sodium carbonate, potassium acetate, sodium acetate or the like. A solvent such as dimethylformamide, ethanol, water or the like can be used alone or in combination. The reaction is usually carried out at room temperature to 100° C. Occasionally, dehydrobromination can be carried out before the solvolysis and then the nitrile is subjected to the solvolysis.

The compound [I] can be prepared by hydrolyzing a compound of the formula:

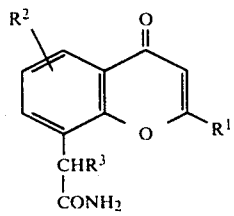

[IX]

wherein each symbol has the meaning given above. This reaction can be carried out by a similar manner to the hydrolysis of the compound [VIII] as shown above.

The compound [I] thus obtained can be isolated and purified with conventional separation techniques such as recrystallization, distillation, chromatography and the like. When the compound [I] is obtained as the free carboxylic acid, it can be converted into its derivatives at the carboxyl group according to a known method.

For example, the carboxylic acid [I] can be converted into a salt, for example, by neutralization and the like.

The carboxylic acid [I] can be converted into an ester, for example, by esterification with an alcohol in the presence of an acid; or by reaction of the acid [I] and an carboxylic acid activating agent, and then reaction of the resultant and an alcohol. Further, the carboxylic acid [I] can be converted into an amide, for example, by reaction with an amine; or by reaction of the acid [I] and an carboxylic acid activating agent, and then reaction of the resultant and an amine. Examples of the carboxylic acid activating agent include thionyl halides (e.g., thionyl chloride, thionyl bromide, etc.), ethyl halogeno carbonate (e.g., ethyl chlorocarbonate, etc.), carbodiimidazole, hydroxysuccinimide, diphenylphosphoryl azide and the like.

On the other hand, the derivative at the carboxylic group of the compound [I] can be converted into another derivative or the free carboxylic acid according to a known method.

For example, the free carboxylic acid can be obtained by hydrolysis in the presence of an alkali or acid. The ester can be converted into an amide by reaction with an amine.

The compound [I] has excellent antitumor activity and can be administered to mammal inclusive of human as an antitumor agent.

Toxicity of the compound [I] is low. For example, when [2-(1-cyclohexenyl)-4-oxo-4H-[1]-benozopyran-8-yl]acetic acid of Example 1 hereinafter was administered to mice, no mouse died at the dosage of 300 mg/kg, p.o. or 200 mg/kg I.P.

When the compound [I] is administered, usually, it is formulated into a pharmaceutical composition together with a pharmacologically acceptable carrier or excipient and administered orally or parenterally.

As a pharmaceutical composition for oral administration, the composition can be in the form of, for example, solid or liquid. Specific examples thereof include tablets, pills, granules, powder, capsules, syrups, emulsions, suspensions and the like. Such a composition can be prepared according to a known method and examples of a carrier or excipient usually used in the pharmaceutical art include lactose, starch, sucrose, magnesium stearate and the like.

As a pharmaceutical composition for parenteral administration, the composition can be in the form of, for example, an injectable preparation or suppository. Examples of the injectable preparation include intravenous injectable liquid, subcutaneous injectable liquid, intradermal injectable liquid, intramuscular injectable liquid, drip injection and the like. Such an injectable preparation can be prepared according to a known method. For example, it is prepared by dissolving, suspending or emulsifying the compound [I] in a sterile aqueous liquid or an oily liquid usually used for an injectable preparation. As an aqueous liquid for injection, there can be used a physiological saline solution, an isotonic solution containing glucose or other adjuvants or the like, and such a solution can contain a suitable solubilizing agent such as an alcohol, a polyalcohol, a nonionic surfactant or the like. As an oily liquid, there can be used sesame oil, soy bean oil or the like and such a solution can contain as a solubilizing agent benzyl benzoate, benzyl alcohol or the like. Usually, an injectable liquid thus prepared is filled in a suitable ampoule to provide an injectable preparation. A suppository used for intrarectal administration can be prepared according to a known method. For example, the compound [I] is admixed with a conventional suppository base and then molded to obtain a suppository.

Each composition as described above can further contain another active ingredient so far as it does not exert undesirable activity due to mixing with the compound [I].

The manner and route of administration as well as the dosage can be suitably chosen according to particular patient and condition to be treated. However, usually, the amount is about 0.01 to 200 mg/kg body weight, preferably, about 0.1 to 100 mg/kg body weight, more preferably, about 10 to 100 mg/kg body weight as the compound [I].

Regarding frequency of administration, the active ingredient can be administered one to three times per day, or at every 2 to 7 days. Further, it is possible to administer an intravenous drip injection with taking a long period of time to maintain a necessary concentration of the active ingredient at a tissue for a long period of time.

The following Reference Examples, Examples and Tests further illustrate the present invention in detail but are not to be construed to limit the scope thereof.

REFERENCE EXAMPLE 1

2-Acetyl-6-methylphenyl cyclohexanecarboxylate

2-Acetyl-6-methylphenol (3.0 g) was dissolved in pyridine (15 ml) and to the solution was added dropwise cyclohexanecarbonyl chloride (3.08 g) with stirring at room temperature. After stirring for 4 hours, the reaction mixture was poured into cold water and extracted with ethyl acetate. The extract was washed with water, diluted hydrochloric acid and then water and dried ($MgSO_4$). The solvent was distilled off under reduced pressure to obtain the title compound (5.2 g) as oil in a quantitative yield.

IR (neat) $cm^{-1}$: 1655, 1590.

NMR ($CDCl_3$) δ: 1.2–2.3 (10H, m), 2.17 (3H, s), 2.4–2.8 (1H, m), 2.52(3H, s), 7.11–7.67 (3H, m).

REFERENCE EXAMPLE 2

2-Acetyl-4-chloro-6-methylphenyl cyclohexanecarboxylate

According to the same manner as described in Reference Example 1, the title compound was obtained from 2-acetyl-4-chloro-6-methylphenol (9.23 g, 0.05 mole) and cyclohexanecarbonyl chloride (8.06 g, 0.055 mole). The product was recrystallized from methanol to obtain prisms (12.5 g), m.p. 74°–75° C., yield 85.0%.

IR (nujol) $cm^{-1}$: 1750, 1680.

NMR ($CDCl_3$) δ: 1.1–2.2 (10H, m), 2.18 (3H, s), 2.53 (3H, s), 2.6 (1H, m), 7.40 (1H, d, J=2 Hz), 7.59 (1H, d, J=2 Hz).

REFERENCE EXAMPLE 3

2-Acetyl-6-methylphenyl 2-propylpentanoate

According to the same manner as described in Reference Example 1, the title compound was obtained from 2-actyl-6-methylphenol and 2-(propyl)pentanoyl chloride , b.p. 120°–125° C./0.5 mmHg, yield 85.8%.

IR (neat) $cm^{-1}$: 1760, 1695.

NMR ($CDCl_3$) δ: 0.8–2.1 (14H, m), 2.18 (3H, s), 2.4–2.8 (1H, m), 2.48 (3H, s), 7.13 (1H, t, J=7.5 Hz), 7.33 (1H, dd, J=7.5 Hz, 2 Hz), 7.49 (1H, dd, J=7.5 Hz, 2 Hz).

REFERENCE EXAMPLE 4

1-Cyclohexyl-3-(2-hydroxy-3-methylphenyl)-1,3-propanedione

2-Acetyl-6-methylphenyl cyclohexanecarboxylate (5.2 g) was dissolved in anhydrous tetrahydrofuran (50 ml) and to the solution was added 60% sodium hydride (880 mg) by portions with stirring at room temperature. After stirring under reflux for 2 hours, the mixture was poured into cold water, acidified with acetic acid and then extracted with ethyl acetate. The extract was washed with water, dried ($MgSO_4$) and then concentrated under reduced pressure to obtain the title compound (5.2 g) as crystals in a quantitative yield. The crystals were recrystallized from methanol to obtain the prisms, m.p. 42°–43° C.

IR (nujol) $cm^{-1}$: 1600, 1580.

NMR ($CDCl_3$) δ: 1.2–2.3 (11H, m), 2.29 (3H, s), 6.17 (1H, s), 6.77 (1H, t, J=8 Hz), 7.23–7.56 (2H, m), 12.5 (1H, s), 15.23 (1H, s).

REFERENCE EXAMPLE 5

1-(5-Chloro-2-hydroxy-3-methylphenyl)-3-cyclohexyl-1,3-propanedione

2-Acetyl-4-chloro-6-methylphenyl cyclohexanecarboxylate (12 g, 0.0408 mole) was dissolved in pyridine (60 ml) and to the solution was added KOH powder (3 g, 0.0536 mole) with stirring at 50° C. The stirring was continued for 1 hour. The reaction mixture was cooled and poured into diluted hydrochloric acid and extracted with hexane-ethyl acetate (2:1). The extract was washed with water and dried ($MgSO_4$). The solvent was distilled off under reduced pressure. The residue was treated with cold methanol to obtain the title compound (9.27 g) as crystals, yield 77.3%. The crystals were recrystallized from ethyl acetate and hexane to obtained prisms, m.p. 76°–77° C.

IR (nujol) $cm^{-1}$: 3400 (br), 1675, 1585.

NMR ($CDCl_3$) δ: 1.1–2.1 (11H, m), 2.23 (3H, s), 6.06 (1H, s), 7.24 (1H, d, J=2 Hz), 7.45 (1H, d, J=2 Hz), 12.41 (1H, s), 15.13 (1H, br).

REFERENCE EXAMPLE 6

1-(2-Hydroxy-3-methylphenyl)-4-propyl-1,3-heptanedione

According to the same manner as described in Reference Example 5, the title compound was obtained as oil from 2-acetyl-6-methylphenyl 2-propylpentanoate in a quantitative yield.

IR (neat) $cm^{-1}$: 1760, 1705, 1730 (s), 1610, 1590.

NMR ($CDCl_3$) δ: 0.8–2.2 (14H, m), 2.2–2.6 (1H, m), 2.23 (3H, s), 6.10 (1H, s), 6.73 (1H, t, J=7.5 Hz), 7.28 (1H, dd, J=7.5 Hz, 2 Hz), 7.48 (1H, dd, J=7.5 Hz, 2 Hz), 12.33 (1H, s), 15.05 (1H, s).

REFERENCE EXAMPLE 7

1-Cyclopentyl-3-(2-hydroxy-3-methylphenyl)-1,3-propanedione

2-Acetyl-6-methylphenyl cyclopentanecarboxylate (24.7 g) obtained from 2-acetyl-6-methylphenol (15 g, 0.1 mole) and cyclopentanecarbonyl chloride (14.2 g, 0.11 mole) according to the same manner as described in Reference Example 1 was dissolved in pyridine (70 ml) and to the solution was added KOH powder (7.28 g, 0.13 mole) at once with stirring at 60° C. The stirring was continued for 30 minutes. The reaction mixture was poured into diluted hydrochloric acid and extracted with ethyl acetate. The extract was washed with water and dried (MgSO$_4$). The solvent was distilled off under reduced pressure. The residue was purified by silica gel column chromatography (eluent: hexane-ethyl acetate (4 : 1)) to obtain the title compound (14.4 g) as crystals, yield 58.5%. The crystals were recrystallized from ethyl acetate and hexane to obtain prisms, m.p. 74°–75° C.

IR (nujol) cm$^{-1}$: 3300 (br), 1665, 1590.

NMR (CDCl$_3$) δ: 1.5–2.1 (8H, m), 2.23 (3H, s), 2.5–3.0 (1H, m), 6.17 (1H, s), 6.73 (1H, t, J=8 Hz), 7.27 (1H, dd, J=8 Hz, 2 Hz), 7.49 (1H, dd, J=8 Hz, 2 Hz), 12.47 (1H, s), 15.23 (1H, br).

REFERENCE EXAMPLE 8

1-Cycloheptyl-3-(2-hydroxy-3-methylphenyl)-1,3-propanedione

2-Acetyl-6-methylpheyl cycloheptanecarboxylate was obtained from 2-acetyl-6-methylphenol (15 g) and cycloheptanecarbonyl chloride (16. 9 g) according to the same manner as described in Reference Example 1 and the title compound was prepared from this compound according to the same manner as described in Reference Example 5. The product was purified by silica gel column chromatography (eluent: hexane-ethyl acetate (4:1)) to obtain an oil (17.8 g).

IR (neat) cm$^{-1}$: 3320 (br), 1660, 1600, 1560.

NMR (CDCl$_3$) δ: 1.4–2.2 (12H, m), 2.2–2.5 (1H, m), 2.23 (3H, s), 6.12 (1H, s), 6.73 (1H, t, J=8 Hz), 7.33 (1H, dd, J=8 Hz, 2 Hz), 7.48 (1H, dd, J=8 Hz, 2 Hz), 12.33 (1H, s), 15.09 (1H, br).

REFERENCE EXAMPLE 9

1-(5-Chloro-2-hydorxy-3-methylphenyl)-3-cyclohexyl-1,3-propanedione

2-Acetyl-4-chloro-6-methylphenol (1.84 g) and methyl cyclohexanecarboxylate (1.7 g) were dissolved in toluene (36 ml) and to the solution was added 60% sodium hydride (0.96 g). Then, the mixture was heated under reflux for 16 hours. The mixture was poured into cold water. Diluted hydrochloric acid was added and crystals precipitated were filtered and recrystallized from methanol to obtain the title compound, yield 1.54 g (52.2%). The melting point and IR and NMR spectra were identical with those of the compound of Reference Example 5.

REFERENCE EXAMPLE 10

2-Cyclohexyl-8-methyl-4-oxo-4H-[1]-benzopyran

1-Cyclohexyl-3-(2-hydroxy-3-methylphenyl)-1,3-propanedione (5.2 g) was dissolved in dichloromethane (50 ml). Trifluoroacetic acid (4 ml) was added to the solution and the mixture was stirred at room temperature for 2 hours. The reaction mixture was concentrated under reduced pressure and then extracted with ethyl acetate. The extract was washed with water, saturated aqueous sodium bicarbonate and then water and dried (MgSO$_4$). The solvent was distilled off under reduced pressure and the residue was purified by silica gel column chromatography (eluent: hexane-ethyl acetate (4:1)) to obtain the title compound as crystals. The crystals were recrystallized from ethyl acetate and hexane to obtain prisms (3.66 g), m.p. 108°–109° C., yield 75.6%.

IR (nujol) cm$^{-1}$: 1640.

NMR (CDCl$_3$) δ: 1.2–2.3 (10H, m), 2.4–2.7 (1H, m), 2.49 (3H, s), 6.17 (1H, s), 7.22 (1H, t, J=8 Hz), 7.45 (1H, dd, J=8 Hz, 2 Hz), 8.04 (1H, dd, J=8 Hz, 2 Hz).

REFERENCE EXAMPLE 11

6-Chloro-2-cyclohexyl-8-methyl-4-oxo-4H-[1]-benzopyran

According to the same manner as described in Reference Example 10, the title compound as crystals was obtained from 1-(5-chloro-2-hydroxy-3-methylphenyl)-3-cyclohexyl-1,3-propanedione (2.95 g) and trifluoroacetic acid (3 ml). The crystals were recrystallized from ethyl acetate and hexane to obtain prisms (2.52 g), yield 91.9%, m.p. 93°–94° C.

IR (nujol) cm$^{-1}$: 1640, 1580.

NMR (CDCl$_3$) δ: 1.2–2.6 (11H, m), 2.47 (3H, s), 6.17 (1H, s), 7.42 (1H, d, J=2 Hz), 7.99 (1H, d, J=2 Hz).

REFERENCE EXAMPLE 12

2-Cyclopentyl-8-methyl-4-oxo-4H-[1]-benzopyran

1-Cyclopentyl-3-(2-hydroxy-3-methylphenyl)-1,3-propanedione (14 g) was dissolved in acetic acid (70 ml) and conc. sulfuric acid (3 ml) was added to the solution. The mixture was stirred at 100° C. for 1 hour. The reaction mixture was poured into cold water and extracted with ethyl acetate. The extract was washed with water, aqueous saturated sodium bicarbonate and then water and dried (MgSO$_4$). The solvent was distilled off under reduced pressure and the residue was purified by silica gel column chromatography (eluent: hexane-ethyl acetate (4:1)) to obtain the title compound (12.7 g) as crystals, yield 97.4%. The crystals were recrystallized from methanol to obtain prisms, m.p. 51°–52° C.

IR (nujol) cm$^{-1}$: 1640, 1595, 1580.

NMR (CDCl$_3$) δ: 1.6–2.3 (8H, m), 2.56 (3H, s), 2.9–3.3 (1H, m), 6.20 (1H, s), 7.23 (1H, t, J=8 Hz), 7.46 (1H, dd, J=8 Hz, 2 Hz), 8.02 (1H, dd, J=8 Hz, 2 Hz).

REFERENCE EXAMPLE 13

2-Cycloheptyl-8-methyl-4-oxo-4H-[1]-benzopyran

According to the same manner as described in Reference Example 12, the title compound as crystals (13.34 g) was obtained from 1-cycloheptyl-3-(2-hydroxy-3-methylphenyl)-1,3-propanedione (17.6 g), yield 81.3%. The crystals were recrystallized from hexane to obtain prisms, m.p. 67°–68° C.

IR (nujol) cm$^{-1}$: 1640, 1595, 1580.

NMR (CDCl$_3$) δ: 1.4–2.2 (12H, m), 2.47 (3H, s), 2.5–2.9 (1H, m), 6.16 (1H, s), 7.20 (1H, t, J=8 Hz), 7.44 (1H, dd, J=8 Hz, 2 Hz), 8.01 (1H, dd, J=8 Hz, 2 Hz).

REFERENCE EXAMPLE 14

2-(1-Propylbutyl)-8-methyl-4-oxo-4H-[1]-benzopyran

According to the same manner as described in Reference Example 12, the title compound was obtained from 1-(2-hydroxy-3-methylphenyl)-4-propyl-1,3-heptanedione, b.p. 140°–152° C./0.5 mmHg, yield 76.9%.

IR (neat) cm$^{-1}$: 1660, 1590.

NMR (CDCl$_3$) δ: 0.90 (6H, t, J=6.8 Hz), 1.1–1.9 (8H, m), 2.25–2.75 (1H, m), 2.47 (3H, s), 6.17 (1H, s), 7.23 (1H, t, J=7.5 Hz), 7.48 (1H, dd, J=7.5 Hz, 2 Hz), 8.05 (1H, dd, J=7.5Hz, 2 Hz).

Elemental Analysis for C$_{17}$H$_{22}$O$_2$,
Calcd: C, 79.03; H, 8.58.
Found: C, 79.20; H, 8.68.

REFERENCE EXAMPLE 15

2-(1-Bromocyclohexyl)-8-bromomethyl-4-oxo-4H-[1]-benzopyran

2-Cyclohexyl-8-methyl-4-oxo-4H-[1]-benzopyran (9.30 g, 0.03 mole), N-bromosuccinimide (14.95 g, 0.084 mole) and α,α'-azobisisobutyronitrile (AIBN) (0.2 g) were added to benzene (150 ml) and the mixture was heated under reflux for 2 hours. After cooling, water was added and benzene layer was separated. The benzene layer was washed with water, dried (MgSO$_4$) and concentrated under reduced pressure to obtain crude crystals. They were recrystallized from ethyl acetate to obtain the title compound as prisms (11.2 g), yield 73.5%, m.p. 134°–135° C.

IR (nujol) cm$^{-1}$: 1640.

NMR (CDCl$_3$) δ: 1.2–2.7 (10H, m), 4.74 (2H, s), 6.49 (1H, s), 7.37(1H, t, J=8 Hz), 7.74 (1H, dd, J=8 Hz, 2 Hz), 8.18 (1H, dd, J=8 Hz, 2 Hz).

Elemental Analysis for C$_{16}$H$_{16}$Br$_2$O$_2$, Calcd: C, 48.03; H, 4.03. Found: C, 47.63; H, 3.99.

REFERENCE EXAMPLE 16

2-(1-Bromocyclohexyl]-8-bromomethyl-6-chloro-4-oxo-4H-[1]-benzopyran

According to the same manner as described in Reference Example 15, the title compound was obtained as crystals (7.59 g) was obtained from 6-chloro-2-cyclohexyl-8-methyl-4-oxo-4H-[1]-benzopyran (6.64 g), yield 72.8%. The crystals were recrystallized from chloroform and methanol to obtain prisms, m.p. 124°–125° C.

IR (nujol) cm$^{-1}$: 1645, 1590, 1580.

NMR (CDCl$_3$) δ: 1.2–2.7 (10H, m), 4.67 (2H, s), 6.47 (1H, s), 7.68 (1H, d, J=2 Hz), 8.11 (1H, d, J=2 Hz).

REFERENCE EXAMPLE 17

2-(1-Bromocyclopentyl)-8-bromomethyl-4-oxo-4H-[1]-benzopyran

According to the same manner as described in Reference Example 15, the title compound was obtained from 2-cyclopentyl-8-methyl-4-oxo-4H-[1]-benzopyran (14.4 g), yield 9.43 g (40.6%). The product was recrystallized from ethyl acetate and hexane to obtain prisms, m.p. 114°–116° C.

IR (nujol) cm$^{-1}$: 1640.

NMR (CDCl$_3$) δ: 1.7–2.8 (8H, m), 4.75 (2H, s), 647 (1H, s), 7.37 (1H, t, J=8 Hz), 7.71 (1H, dd, J=8 Hz, 2 Hz), 8.14 (1H, dd, J=8Hz, 2 Hz).

REFERENCE EXAMPLE 18

2-(1-Bromocycloheptyl)-8-bromomethyl-4-oxo-4H-[1]-benzopyran

According to the same manner as described in Reference Example 15, the title compound was obtained from 2-cycloheptyl-8-methyl-4-oxo-4H-[1]-benzopyran (13.2 g), yield 11.17 g (50.1%), m.p. 90°–91° C.

IR (nujol) cm$^{-1}$: 1670, 1655.

NMR (CDCl$_3$) δ: 1.3–2.0 (8H, m), 2.5–2.9 (4H, m), 4.73 (2H, s), 6.51 (1H, s), 7.36 (1H, t, J=8 Hz), 7.71 (1H, dd, J=8 Hz, 2 Hz), 8.14 (1H, dd, J=8 Hz, 2 Hz).

REFERENCE EXAMPLE 19

2-(1-Bromo-1-propylbutyl)-8-bromomethyl-4-oxo-4H-[1]-benzopyran

According to the same manner as described in Reference Example 15, the title compound was obtained from 2-(1-propylbutyl)-8-methyl-4-oxo-4H-[1]-benzopyran and N-bromosuccinimide, m.p. 86°–87° C., yield 58.7%.

IR (KBr) cm$^{-1}$: 1645.

NMR (CDCl$_3$) δ: 0.97 (6H, t, J=6.8 Hz), 1.2–1.7 (4H, m), 2.2–2.4 (4H, m), 4.72 (2H, s), 6.62 (1H, s), 7.33 (1H, t, J=7.5 Hz), 7.71 (1H, dd, J=7.5 Hz, 2 Hz), 8.15 (1H, dd, J=7.5 Hz, 2 Hz).

Elemental Analysis for C$_{17}$H$_{20}$O$_2$Br$_2$, Calcd: C, 49.07; H, 4.84. Found: C, 49.06; H, 4.73.

REFERENCE EXAMPLE 20

2-(1-Bromocyclohexyl]-8-cyanomethyl-4-oxo-4H-[1]-benzopyran 2-(1-Bromocyclohexyl)-8-bromomethyl-4-oxo-4H-[1]-benzopyran (11.2 g, 0.028 mole) was dissolved in dimethylformamide (200 ml) and to the solution was added NaCN (1.5 g, 0.0305 mole) with stirring at 10° C. The mixture was stirred for 30 minutes. Water was added to the reaction mixture and crystals precipitated were filtered off. The crude crystals were purified by silica gel chromatography (eluent: chloroform-hexane (10:1)) to obtain the title compound (4.08 g), yield 44.7 %. The product was recrystallized from ethyl acetate to obtain prisms, m.p. 144°–145° C.

IR (nujol) cm$^{-1}$: 2240, 1640.

NMR (CDCl$_3$) δ: 1.2–2.7 (10H, m), 3.97 (2H, s), 6.44 (1H, s), 7.40 (1H, t, J=8 Hz), 7.44 (1H, dd, J=8 Hz, 2 Hz), 8.17 (1H, dd, J=8 Hz, 2 Hz).

Elemental Analysis for C$_{17}$H$_{16}$BrNO$_2$, Calcd: C, 58.98; H, 4.66; N, 4.05. Found: C, 59.07; H, 4.65; N, 4.06.

REFERENCE EXAMPLE 21

2-(1-Bromocyclohexyl)-8-cyanomethyl-4-oxo-4H-[1]-benzopyran

NaCN (3.88 g, 0.075 mole) was dissolved in water (11 ml) and to the solution was added benzyltrimethylammonium chloride (13.9 g, 0.075 mole). After stirring at 50° C. for 15 minutes, chloroform (120 ml) was added and further 2 -(1-bromocyclohexyl)-8-bromomethyl-4-oxo-4H-[1]-benzopyran (12 g, 0.03 mole) was added. The mixture was stirred for 4 hours. The chloroform layer was washed with water, dried (MgSO$_4$) and then concentrated under reduced pressure to obtain crystals. The crude crystals were recrystallized from ethyl acetate to obtain the title compound (7.5 g) as prisms, m.p. 143°–144° C., yield 72.2%. IR and NMR spectra of this compound were identical with those of the compound obtained in Reference Example 20.

REFERENCE EXAMPLE 22

2-(1-Bromocyclohexyl)-6-chloro-8-cyanomethyl-4-oxo-4H-[1]-benzopyran

According to the same manner as described in Reference Example 21, the title compound was obtained from 2-(1-bromocyclohexyl)-8-bromomethyl-6-chloro-4-oxo-4H-[1]-benzopyran, yield 53.9%. The product was recrystallized from ethyl acetate and hexane to obtain prisms, m.p. 122°–123° C.

IR (nujol) cm$^{-1}$: 2240, 1660, 1640, 1590, 1580.

NMR (CDCl$_3$) δ: 1.0–2.6 (10H, m), 3.98 (2H, s), 6.47 (1H, s), 7.41 (1H, d, J=2 Hz), 8.14 (1H, d, J=2 Hz).

REFERENCE EXAMPLE 23

2-(1-Bromocyclopentyl)-8-cyanomethyl-4-oxo-4H-[1]-benzopyran

According to the same manner as described in Reference Example 21, the title compound was obtained from 2-(1-bromocyclopentyl)-8-bromomethyl-4-oxo-4H-[1]-benzopyran, yield 62.2%, m.p. 132°–133° C.

IR (nujol) cm$^{-1}$: 2230, 1640, 1595, 1580.

NMR (CDCl$_3$) δ: 1.9–2.8 (8H, m), 4.00 (2H, s), 6.47 (1H, s), 7.44 (1H, t, J=8 Hz), 7.8 (1H, dd, J=8 Hz, 2 Hz), 8.2 (1H, dd, J=8 Hz, 2 Hz).

REFERENCE EXAMPLE 24

2-(1-Bromocycloheptyl)-8-cyanomethyl-4-oxo-4H-[1]-benzopyran

According to the same manner as described in Reference Example 21, the title compound was obtained from 2-(1-bromocycloheptyl)-8-bromomethyl-4-oxo-4H-[1]-benzopyran, yield 68.8%. The product was recrystallized from ethyl acetate to obtain prisms, m.p. 97°–98° C.

IR (nujol) cm$^{-1}$: 2230, 1660, 1595, 1580.

NMR (CDCl$_3$) δ: 1.4–1.9 (8H, m), 2.5–2.7 (4H, m), 4.00 (2H, s), 6.51 (1H, s), 7.46 (1H, t, J=8 Hz), 7.91 (1H, dd, J=8 Hz, 2 Hz), 8.22 (1H, dd, J=8 Hz, 2 Hz).

REFERENCE EXAMPLE 25

2-(1-Bromo-1-propylbutyl)-8-cyanomethyl-4-oxo-4H-[1]-benzopyran

According to the same manner as described in Reference Example 21, the title compound was obtained from 2-(1-bromo-1-propylbutyl)-8-bromomethyl-4-oxo-4H-[1]-benzopyran, m.p. 120°–122° C. (recrystallized from ethyl acetate), yield 83%.

IR (KBr) cm$^{-1}$: 2250, 1655.

NMR (CDCl$_3$) δ: 0.97 (6H, t, J=6.8 Hz), 1.2–1.7 (4H, m), 2.2–2.4 (4H, m), 3.95 (2H, s), 6.53 (1H, s), 7.42 (1H, t, J=&.5 Hz), 7.77 (1H, dd, J=7.5 Hz, 2 Hz), 8.20 (1H, dd, J=7.5 Hz, 2 Hz).

Elemental Analysis for C$_{18}$H$_{20}$NO$_2$Br, Calcd: C, 59.68; H, 5.56; N, 3.87. Found: C, 59.52; H, 5.26; N, 3.76.

EXAMPLE 1

[2-(1-Cyclohexenyl)-4-oxo-4H-[1]-benzopyra-8-yl]acetic acid 2-(1-Bromocyclohexyl)-8-cyanomethyl-4-oxo-4H-[1]-benzopyran (7.0 g) was dissolved in acetic acid (70 ml) and to the solution was added 50% sulfuric acid (70 ml). The mixture was stirred at 110° C. for 4 hours. The reaction mixture was diluted with cold water and crystals deposited was filtered off. The cyrstals were recrystallized from ethyl acetate and methanol to obtain the title compound (4.24 g) as prisms, m.p. 214°–216° C., yield 73.7%.

IR (nujol) cm$^{-1}$: 2500–3000, 1730, 1620, 1585.

NMR (d$_6$-DMSO) δ: 1.5–1.9 (4H, m), 2.1–2.4 (4H, m), 3.87 (2H, s), 6.28 (1H, s), 6.87–7.07 (1H, m), 7.36 (1H, t, J=8 Hz), 7.69 (1H, dd, J=8 Hz, 2 Hz), 7.88 (1H, dd, J=8 Hz, 2 Hz).

Elemental Analysis for C$_{17}$H$_{16}$O$_4$, Calcd: C, 71.82; , 5.67. Found: C, 71.86; H, 5.65.

EXAMPLE 2

[6-Chloro-2-(1-cyclohexenyl)-4-oxo-4H-[1]-benzopyran-8-yl]acetic acid

According to the same manner as decribed in Example 1, the title compound was obtained from 2-(1-bromocyclohexyl)-6-chloro-8-cyanomethyl-4-oxo-4H-[1]-benzopyran, yield 70.9%. The product was recrystallized from dichloromethane and methanol to obtain prisms, m.p. 204°–206° C.

IR (nujol) cm$^{-1}$: 2500–3000, 1715, 1620, 1575.

NMR (d$_6$-DMSO) δ: 1.4–1.8 (4H, m), 2.1–2.4 (4H, m), 3.91 (2H, s), 6.33 (1H, s), 6.97 (1H, m), 7.77–7.88 (2H, m), 12.7 (1H, br).

Elemental Analysis for C$_{17}$H$_{15}$ClO$_4$, Calcd: C, 64.06; H, 4.74. Found: C, 64.17; H, 4.60.

EXAMPLE 3

[2-(1-Cyclopentenyl)-4-oxo-4H-[1]-benzopyran-8-yl]acetic acid

According to the same manner as described in Example 1, the title compound was obtained from 2-(1-bromocyclopentyl)-8-cyanomethyl-4-oxo-4H-[1]-benzopyran, yield 70.9%. The product was recrystallized from dichloromethane and methanol to obtain needles, m.p. 198°–200° C.

IR (nujol) cm$^{-1}$: 2500–3000, 1740, 1715, 1630, 1610, 1580.

NMR (d$_6$-DMSO) δ: 1.9–2.2 (2H, m), 2.5–2.7 (4H, m), 3.91 (2H, s), 6.28 (1H, s), 6.86 (1H, m), 7.38 (1H, t, J=8 Hz), 7.71 (1H, dd, J=8 Hz, 2 Hz), 7.93 (1H, dd, J=8 Hz, 2 Hz).

Elemental Analysis for C$_{16}$H$_{14}$O$_4$, Calcd: C, 71.10; H, 5.22. Found: C, 70.82; H, 5.04.

EXAMPLE 4

[2-(1-Cycloheptenyl)-4-oxo-4H-[1]-benzopyran-8-acetic acid

According to the same manner as described in Example 1, the title compound was obtained from 2-(1-bromocycloheptyl)-8-cyanomethyl-4-oxo-4H-[1]-benzopyran, yield 73.5%. The product was recrystallized from methanol to obtain needles, m.p. 168°–170° C.

IR (nujol) cm$^{-1}$: 2500–3000, 1720, 1610, 1580.

NMR (d$_6$-DMSO) δ: 1.4–1.9 (6H, m), 2.3–2.7 (4H, m), 3.93 (2H, s), 6.42 (1H, s), 7.06 (1H, t, J=7 Hz), 7.39 (1H, t, J=8 Hz), 7.71 (1H, dd, J=8 Hz, 2 Hz), 7.93 (1H, dd, J=8 Hz, 2 Hz), 12.7 (1H, br).

EXAMPLE 5

[2-(3-Hepten-4-yl)-4-oxo-4H-[1]-benzopyran-8-yl]acetic acid

According to the same manner as described in Example 1, the title compound was obtained from 2-(1-bromo-1-propylbutyl)-8-cyanomethyl-4-oxo-4H-[1]-benzopyran, m.p. 216°–218° C. (recrystallized from 80% ethanol), yield 68%.

IR (KBr) cm$^{-1}$: 2300–3000, 1720, 1610, 1580.

NMR (d$_6$-DMSO) δ: 0.8–1.6 (8H, m), 2.1–2.6 (4H, m), 3.90 (2H, s), 6.40 (1H, s), 6.67 (1H, t, J=7.5 Hz), 7.37 (1H, t, J=7.5 Hz), 7.70 (1H, dd, J=7.5 Hz, 2 Hz), 7.92 (1H, dd, J=7.5 Hz, 2 Hz), 12.5 (1H, br, s).

Elemental Analysis for C$_{18}$H$_{20}$O$_4$, Calcd: C, 71.98; H, 6.71. Found: C, 72.06; H, 6.71.

EXAMPLE 6

[2-(1-Cyclohexenyl)-4-oxo-4H-[1]-benzopyran-8-yl]acetamide

[2-(1-cyclohexenyl)-4-oxo-4H-[1]-benzopyran-8-yl]acetic acid (100 mg) and triethylamine (53 mg) were added to dichloromethane (2ml). After addition of diphenylphosphoryl azide (145 mg) with stirring under ice cooling, the mixture was stirred at room temperature for 1 hour. Conc. aqueous ammonia (5 ml) was added to the reaction mixture and stirring was further continued for 1 hour. Hexane (5 ml) was added and crystals deposited were filtered off. The crystals were recrystallized from dichloromethane and methanol to obtain the title compound as needles, m.p. 244°–245° C., yield 64 mg (64.6%).

IR (nujol) cm$^{-1}$: 3400, 3310, 3220, 1670, 1625.

NMR (d$_6$-DMSO) δ: 1.5–1.8 (4H, m), 2.2–2.4 (4H, m), 3.73 (2H, s), 6.27 (1H, s), 6.97 (1H, br), 7.07 (1H, m), 7.33 (1H, t, J=8 Hz), 7.5 (1H, br), 7.63 (1H, dd, J=8 Hz, 2 Hz), 7.89 (1H, dd, J=8 Hz, 2 Hz).

Elemental Analysis for C$_{17}$H$_{17}$NO$_3$, Calcd: C, 72.07; H, 6.05; N, 4.94. Found: C, 72.00; H, 5.86; N, 4.78.

EXAMPLE 7

Sodium 2-(1-cyclohexenyl)-4-oxo-4H-[1]-benzopyran-8-yl]acetate

[2-(1-Cyclohexenyl)-4-oxo-4H-[1]-benzopyran-8-yl]acetic acid (200 mg) was dissolved in a mixed solvent of chloroform (9 ml) and methanol (1 ml). After addition of a 1N solution of NaOMe in methanol (0.7 ml), the solution was concentrated under reduced pressure. The residue was dissolved in methanol and acetone was added to the solution to obtain the title compound as crystals, m.p. 260°–265° C. (dec), yield 183 mg (78.4%).

IR (nujol) cm$^{-1}$: 3300, 2500–3000, 1625, 1585.

NMR (d$_6$-DMSO) δ: 1.5–1.8 (4H, m), 2.2–2.4 (4H, m), 3.47 (2H, s), 6.22 (1H, s), 7.1 (1H, m), 7.27 (1H, t, J=8 Hz), 7.56 (1H, dd, J=8 Hz, 2 Hz), 7.78 (1H, dd, J=8 Hz, 2 Hz).

Elemental Analysis for C$_{17}$H$_{15}$O$_4$Na.1.5 H$_2$O, Calcd: C, 61.26; H, 5.44. Found: C, 61.39; H, 5.50.

EXAMPLE 8

Ethyl [2-(1-cyclohexenyl)-4-oxo-4H-[1]-benzopyran-8-yl]acetate

[2-(1-Cyclohexenyl)-4-oxo-4H-[1]-benzopyran-8-yl]acetic acid (2.0 g) was dissolved in ethanol (50 ml) and to the solution was added conc. sulfuric acid (0.5 ml). The mixture was heated under reflux for 5 hours. After dilution with water, the mixture was extracted with ethyl acetate and the extract was washed with water, dried (MgSO$_4$) and concentrated under reduced pressure to obtain the title compound as crystals. The crystals were recrystallized from ethyl acetate to obtain prisms, yield 1.34 g (61.0%), m.p. 126°–127° C.

IR (nujol) cm$^{-1}$: 1725, 1640, 1590, 1575.

NMR (CDCl$_3$) δ: 1.23 (3H, t, J=7 Hz), 1.5–1.9 (4H, m), 2.2–2.4 (4H, m), 3.87 (2H, s), 4.17 (2H, q, J=7 Hz), 6.3 (1H, s), 6.96 (1H, m), 7.31 (1H, t, J=8 Hz), 7.57 (1H, dd, J=8 Hz, 2 Hz).

Elemental Analysis for C$_{19}$H$_{20}$O$_4$, Calcd: C, 73.06; H, 6.45. Found: C, 72.92; H, 6.48.

EXAMPLE 9

N-Methyl-[2-(1-cyclohexenyl)-4-oxo-4H-[1]-benzopyran-8-yl]acetamide

[2-(1-Cyclohexenyl)-4-oxo-4H-[1]-benzopyran-8-yl]acetic acid (568 mg) and triethylamine (0.34 ml) were added to dichloromethane (6 ml) and to the mixture was added dropwise diphenylphosphoryl azide (0.52 ml) with stirring at room temperature. After stirring for 30 minutes, 30% aqueous methylamine solution (5 ml) was added and stirring was continued for additional 2 hours. The solvent was distilled off under reduced pressure and n-hexane was added to the residue. Crystals deposited were filtered. The crude crystals were recrystallized from methanol to obtain the title compound as prisms, yield 380 mg (64%), m.p. 213°–214° C.

IR (nujol) cm$^{-1}$: 3290, 3240, 3030, 1660, 1630.

NMR (CDCl$_3$) δ: 1.6–1.9 (4H, m), 2.2–2.4 (4H, m), 3.11 (3H, d, J=5 Hz), 3.80 (2H, s), 5.75 (1H, br), 6.21 (1H, s), 6.93 (1H, m), 7.28 (1H, t, J=8 Hz), 7.56 (1H, dd, J=8 Hz, 2 Hz), 8.03 (1H, dd, J=8 Hz, 2 Hz).

Elemental Analysis for C$_{18}$H$_{19}$NO$_3$, Calcd C, 72.71; H, 6.44; N, 4.71. Found: C, 72.57; H, 6.43; N, 4.74.

EXAMPLE 10

N,N-Dimethyl-[2-(1-cyclohexenyl)-4-oxo-4H-[1]-benzopyran-8-yl]acetamide

According to the same manner as described in Example 9, the title compound was obtained from [2-(1-cyclohexenyl)-4-oxo-4H-[1]-benzopyran-8-yl]acetic acid and triethylaminde, diphenylphosphoryl azide and dimethylamine, yield 72%, m.p. 200°–202° C. (recrystallized from methanol).

IR (nujol) cm$^{-1}$: 1650, 1630.

NMR (CDCl$_3$) δ: 1.6–1.9 (4H, m), 2.2–2.4 (4H, m), 3.00 (3H, s), 3.07 (3H, s), 3.93 (2H, s), 6.28 (1H, s), 6.84 (1H, m), 7.29 (1H, t, J=8 Hz), 7.52 (1H, dd, J=8 Hz, 2 Hz), 8.09 (1H, dd, J=8 Hz, 2 Hz).

Elemental Analysis for C$_{19}$H$_{21}$NO$_3$, Calcd: C, 73.29; H, 6.80; N, 4.50. Found: C, 73.06; H, 6.82; N, 4.45.

EXAMPLE 11

N-Phenyl-[2-(1-cyclohexenyl)-4-oxo-4H-[1]-benzopyran-8-yl]acetamide

According to the same manner as described in Example 9, the title compound was obtained from [2-(1-cyclohexenyl)-4-oxo-4H-[1]-benzopyran-8-yl]acetic acid, triethylamine, diphenylphosphoryl azide and aniline yield 43%, m.p. 242°–243° C. (recrystallized from methanol).

IR (nujol) cm$^{-1}$: 3240, 3200, 3130, 3060, 3040, 1650.

NMR (CDCl$_3$+d$_6$-DMSO) δ: 1.3–1.9 (4H, m), 2.0–2.4 (4H, m), 3.97 (2H, s), 6.19 (1H, s), 6.9–7.75 (8H, m), 7.98 (1H, dd, J=8 Hz, 2 Hz), 10.06 (1H, br).

Elemental Analysis for C$_{23}$H$_{21}$NO$_3$, Calcd: C, 76.86; H, 5.89; N, 3.90. Found: C, 76.60; H, 5.65; N, 3.90.

EXAMPLE 12

N-[2-(Cyclohexenyl)-4-oxo-4H-[1]-benzopyran-8-ylacetyl]morpholine

According to the same manner as described in Example 9, the title compound was obtained from [2-(1-cyclohexenyl)-4-oxo-4H-[1]-benzopyran-8-yl]acetic acid, triethylamine, diphenylphosphoryl azide and morpholine, yield 72%, m.p. 194°–195° C. (recrystallized from methanol).

IR (nujol) cm$^{-1}$: 1635.

NMR (CDCl$_3$) δ: 1.5–2.0 (4H, m), 2.2–2.4 (4H, m), 3.5–3.8 (8H, m), 3.93 (2H, s), 6.30 (1H, s), 6.87 (1H, m), 7.31 (1H, t, J=8 Hz), 7.53 (1H, dd, J=8 Hz, 2 Hz), 8.22 (1H, dd, J=8 Hz, 2 Hz).

Elemental Analysis for C$_{21}$H$_{23}$NO$_4$, Calcd: C, 71.37; H, 6.56; N, 3.96. Found: C, 71.45; H, 6.58; N, 3.87.

EXAMPLE 13

Methyl [2-(1-cyclohexenyl)-4-oxo-4H-[1]-benzopyran-8-yl]acetate

[2-(1-Cyclohexenyl)-4-oxo-4H-[1]-benzopyran-8-yl]acetic acid (1.42 g) and conc. sulfuric acid (0.2 ml) were added to methanol (30 ml) and the mixture was refluxed for 3 hours. Then, water was added. The mixture was extracted with ethyl acetate and the extracted layer was washed and dried. Ethyl acetate was distilled off under reduced pressure and the residue was recrystallized from hexane-ethyl acetate to obtain the title compound, m.p. 137°–138° C., yield 72%.

IR (nujol) cm$^{-1}$: 1730, 1635, 1590, 1570.

NMR (CDCl$_3$) δ: 1.6–1.8 (4H, m), 2.2–2.4 (4H, m), 3.76 (3H, s), 3.90 (2H, s), 6.33 (1H, s), 6.97 (1H, m), 7.33 (1H, t, J=8 Hz), 7.60 (1H, dd, J=8 Hz, 2 Hz), 8.17 (1H, dd, J=8 Hz, 2 Hz).

Elemental Analysis for C$_{18}$H$_{18}$O$_4$, Calcd: C, 72.47; H, 6.08. Found: C, 72.56; H, 6.04.

EXAMPLE 14

Isopropyl [2-(1-cyclohexenyl)-4-oxo-4H-[1]-benzopyran-8-yl]acetate

According to the same manner as described in Example 13, the title compound was obtained from [2-(1-cyclohexenyl)-4-oxo-4H-[1]-benzopyran-8-yl]acetic acid and isopropanol, yield 63%, m.p. 142°–143° C. (recrystallized from hexane-ethyl acetate).

IR (nujol) cm$^{-1}$: 1725, 1635.

NMR (CDCl$_3$) δ: 1.20 (6H, d, J=6 Hz), 1.5–2.0 (4H, m), 2.2–2.5 (4H, m), 3.83 (2H, s), 4.88–5.20 (1H, m), 6.33 (1H, s), 6.93 (1H, m), 7.28 (1H, t, J=8 Hz), 7.60 (1H, dd, J=8 Hz, 2 Hz), 8.11 (1H, dd, J=8 Hz, 2 Hz).

Elemental Analysis for C$_{20}$H$_{22}$O$_4$, Calcd: C, 73.60; H, 6.79. Found: C, 73.43; H, 6.72.

EXAMPLE 15

2,2-Dimethylpropyl [2-(1-cyclohexenyl)-4-oxo-4H-[1]-benzopyran-8-yl)acetate

[2-(1-Cyclohexenyl)-4-oxo-4H-[1]-benzopyran-8-yl]acetic acid (2.84 g) was dissolved in dimethylformamide (30 ml) and carbodiimidazole (1.78 g) was added to the solution. After stirring at room temperature for 2 hours, 2,2-dimethyl-propanol (0.88 g) was added. After stirring at 60° C. for 4 hours, water was added and the mixture was extracted with ethyl acetate. The extracted layer was washed with water, dried and concentrated. The residue was purified by silica gel column chromatography to obtain the title compound (0.82 g), yield 23%, m.p. 138°–139° C. (recrystallized from hexane-ethyl acetate).

IR (nujol) cm$^{-1}$: 1730, 1635.

NMR (CDCl$_3$) δ: 0.80 (9H, s), 1.5–2.0 (4H, m), 2.2–2.5 (4H, m), 3.77 (2H, s), 3.90 (2H, s), 6.28 (1H, s), 6.94 (1H, m), 7.29 (1H, t, J=8 Hz), 7.56 (1H, dd, J=8 Hz, 2 Hz), 8.12 (1H, dd, J=8 Hz, 2 Hz).

Elemental Analysis for C$_{22}$H$_{26}$O$_4$, Calcd: C, 74.55; H, 7.39. Found: C, 74.65; H, 7.42.

EXAMPLE 16

2,2-Dimethyl-1,3-dioxolan-4-ylmethyl [2-(1-cyclohexenyl)-4-oxo-4H-[1]-benzopyran-8-yl]acetate

[2-(1-Cyclohexenyl)-4-oxo-4H-[1]-benzopyran-8-yl]acetic acid (2.84 g), 2,2-dimethyl-1,3-dioxolan-4-methanol (3.96 g) and dicyclohexylcarbodiimide (2.28 g) were added to dichloromethane (30 ml) with ice cooling and then the mixture was stirred at room temperature for 18 hours. The mixture was concentrated under reduced pressure and the residue was purified by silica gel column chromatography to obtain the title compound (2.65 g), yield 67%, m.p. 104°–105° C. (recrystallized from ethyl acetate).

IR (nujol) cm$^{-1}$: 1725, 1645, 1590, 1575.

NMR (CDCl$_3$) δ: 1.34 (6H, s), 1.6–1.8 (4H, m), 2.2–2.4 (4H, m), 3.53–3.76 (2H, m), 3.9–4.35 (3H, m), 3.93 (2H, s), 6.31 (1H, s), 6.93 (1H, m), 7.33 (1H, t, J=8 Hz), 7.61 (1H, dd, J=8 Hz, 2 Hz), 8.11 (1H, dd, J=8 Hz, 2 Hz).

Elemental Analysis for C$_{23}$H$_{26}$O$_6$, Calcd: C, 69.33; H, 6.58. Found: C, 69.41; H, 6.67.

EXAMPLE 17

2,3-Dihydroxypropyl [2-(1-cyclohexenyl)-4-oxo-4H-[1]-benzopyran-8-yl]acetate 2,2-Dimethyl-1,3-dioxolan-4-ylmethyl [2-(1-cyclohexenyl)-4-oxo-4H-[1]-benozopyran-8-yl]acetate (2.0 g) was dissolved in tetrahydrofuran (30 ml) and 2N hydrochloric acid (10 ml) was added. The mixture was stirred at 50° C. for 1 hour and then water was added. The mixture was extracted with chloroform and the extracted layer was washed with water, dried and concentrated. The residue was recrystallized from ethyl acetate to obtain the title compound (1.0 g) as prisms, yield 59%.

IR (nujol) cm$^{-1}$: 3300–3500, 1740, 1640, 1590, 1570.

NMR (CDCl$_3$) δ: 1.6–1.8 (4H, m), 2.2–2.4 (4H, m), 2.13 (1H, t, J=6 Hz), 2.87 (1H, d, J=6 Hz), 3.4–3.7 (2H, m), 3.7–4.0 (1H, m), 3.94 (2H, s), 4.20 (2H, d, J=6 Hz), 6.27 (1H, s), 6.92 (1H, m), 7.30 (1H, t, J=8 Hz), 7.53 (1H, dd, J=8 Hz, 2 Hz), 8.08 (1H, dd, J=8 Hz, 2 Hz).

Elemental Analysis for C$_{20}$H$_{22}$O$_6$, Calcd: C, 67.03; H, 6.19. Found: C, 67.13; H, 6.37.

EXAMPLE 18

[2-(1-Cyclohexenyl)-4-oxo-4H-[1]-benzopyran-8-yl]acetic acid

Ethyl [2-(1-cyclohexenyl)-4-oxo-4H-[1]-benzopyran-8-yl]acetate (2.5 g) was dissolved in acetic acid (35 ml) and to the solution was added 50% sulfulic acid (30 ml). The mixture was refluxed for 4 hours. The reaction mixture was diluted with water and crystals deposited were filtered off and recrystallized from the mixed solvent of ethyl acetate and methanol to obtain the title compound, yield 68%.

The melting point and IR and NMR spectra were identical with those of the product of Example 1.

EXAMPLE 19

[2-(1-Cyclohexenyl)-4-oxo-4H-[1]-benzopyran-8-yl]acetamide 2-(1-Bromocyclohexyl)-8-cyanomethyl-4-oxo-4H-[1]-benzopyran (3.0 g) was added to polyphosphoric acid (120 ml) and the mixture was heated on an oil bath at about 120° C. for 2 hours. After standing overnight, water (about 300 ml) was added to decompose polyphosphoric acid. Crystals deposited were filtered off and recrystallized form the mixed solvent of dichloromethane and methanol to obtain the title compound, yield 57%.

The melting point and IR and NMR spectra were identical with those of the product of Example 6.

EXAMPLE 20

Ethyl [2-(1-cyclohexenyl]-4-oxo-4H-[1]-benzopyran-8-yl]acetate 2-(1-Bromocyclohexyl)-8-cyanomethyl-4-oxo-4H-[1]-benzopyran (5.0 g) and 50% sulfuric acid (4 ml) were added to ethanol (400 ml) and the mixture was refluxed for 8 hours. Then, ethanol (about 300 ml) was distilled off under reduced pressure and the residue was added to water. The mixture was extracted with ethyl acetate and the extract was washed with water, dried (MgSO$_4$) and concentrated. The residue was recrystallized from ethyl acetate to obtain the title compound, yield 56%.

The melting point and IR and NMR spectra were identical with those of the product of Example 8.

EXAMPLE 21

[2-(1-Cyclohexenyl)-4-oxo-4H-[1]-benzopyran-8-yl]acetic acid

[2-(1-Cyclohexenyl)-4-oxo-4H-[1]-beonzopyran-8-yl]acetamide (1.3 g) was added to a mixture of acetic acid (20 ml) and 50% sulfuric acid (20 ml) and the mixture was refluxed for 6 hours. After cooling, the reaction mixture was diluted with water and crystals deposited were filtered and recrystallized from the mixed solvent of ethyl acetate and methanol to obtain the title compound, yield 71%.

The melting point and IR and NMR spectra were identical with those of the product of Example 1.

Test 1

M5076 Tumor cells (1×10$^6$ cells/mouse) were transplanted intraperitoneally into BDF$_1$ mice (5 mice/group). From 24 hours after transplantation, a drug was injected intraperitoneally into mice daily for 9 consecutive days. The antitumor efficacy of the drug was assessed on the basis of prolongation of the survival time of tumor-bearing mice and the percentage of treated (T) versus control (C) (T/C %) calculated from the survival time more than 130% was considered to be active. The results are shown in Table 1.

TABLE 1

| Drug | Dose (mg/kg) | Median survival days | T/C (%) | Number of animals survival for 100 days or more/number of test animals |
| --- | --- | --- | --- | --- |
| Compound [II](supra) | 50 | 51.5 | 242 | 0/5 |
| Compound of Example 1 | 25 | 86.5 | 406 | 2/5 |
| Control | — | 21.3 | 100 | 0/5 |

Test 2

M5076 tumor cells (5×10$^6$ cells/mouse) were transplanted interadermally into the flank of C57BL/6 mice (5 mice/group). From 24 hours after transplantation, a drug was injected intraperitoneally into mice daily for 5 consecutive days. The tumors were excised 7 days after transplantation and the survival time of the mice were observed. The percentage of drug-tested (T) versus tumor-excised control (C) (T/C %) over than 130% was considered to be active. The results are shown in Table 2.

TABLE 2

| Drug | Dose (mg/kg) | Median survival days | T/C (%) | Number of animals survival for 100 days or more/number of test animals |
| --- | --- | --- | --- | --- |
| Compound [II] | 50 | 31.0 | 87 | 0/5 |
| Compound of Example 1 | 50 | 85.5 | 241 | 1/5 |
| Tumor excised control | — | 35.5 | 100 | 0/5 |

Test 3

M5076 tumor cells (5×10$^6$ cells/mouse) were transplanted interadermally into the flank of C57BL/6 mice (5 mice/group). From 24 hours after transplantation, a drug was administered orally to mice daily for 5 consecutive days. The tumors were excised 7 days after transplantation and the survival time of the mice were observed. The percentage of drug-treated (T) versus tumor-excised control (C) (T/C %) over than 130% was considered to be active. The results are shown in Table 3.

TABLE 3

| Drug | Dose (mg/kg) | Median survival days | T/C (%) | Number of animals survival for 100 days or more/number of test animals |
| --- | --- | --- | --- | --- |
| Compound [II] | 100 | 42.5 | 129 | 1/5 |
| Compound of Example 3 | 100 | 76.5 | 232 | 2/5 |
| Compound of Example 13 | 100 | — | >215 | 3/5 |
| Compound of Example 8 | 100 | — | >215 | 3/5 |
| Compound of Example 17 | 100 | 86.5 | 262 | 0/5 |
| Tumor excised control | — | 33.0 | 100 | 0/10 |

Example of Pharmaceutical Composition

According to convention pharmaceutical techniques, capsules, soft capsules and tablets are prepared according to the following formulations.

| (A) Capsules | |
|---|---|
| Ingredients | Amount |
| (1) Compound of Example 1 | 50 mg |
| (2) Very fine powder of cellulose | 30 mg |
| (3) Lactose | 37 mg |
| (4) Magnesium stearate | 3 mg |
| Total | 120 mg |

The ingredients (1) to (4) are mixed and filled in gelating capsules.

| (B) Soft capsules | |
|---|---|
| Ingredients | Amount |
| (1) Compound of Example 3 | 50 mg |
| (2) Corn oil | 100 mg |
| Total | 150 mg |

The ingredients (1) and (2) are mixed and filled in soft capsules.

| (C) Tablets | |
|---|---|
| Ingredients | Amount |
| (1) Compound of Example 1 | 50 mg |
| (2) Lactose | 34 mg |
| (3) Corn starch | 10.6 mg |
| (4) Corn starch (paste) | 5 mg |
| (5) Magnesium stearate | 0.4 mg |
| (6) Calcium carboxymethyl-cellulose | 20 mg |
| Total | 120 mg |

These ingredients are mixed and compressed by a tablet machine.

What is claimed is:

1. A compound of the formula

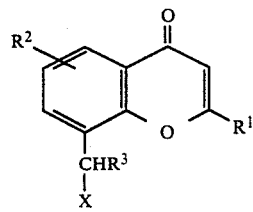

wherein $R^1$ is cycloalkenyl having 3 to 7 carbon atoms; $R^2$ is hydrogen or halogen; $R^3$ is hydrogen or lower alkyl; and X is carboxyl, or a pharmaceutically acceptable salt, ester or amide thereof.

2. A compound according to claim 1, wherein $R^1$ is cycloalkenyl having 5 to 6 carbon atoms.

3. The compound according to claim 2 being [2-(1-cyclohexenyl)-4-oxo-4H-[1]-benzopyran-8-yl]acetic acid, or a pharmaceutically acceptable salt, ester or amide thereof.

4. The compound according to claim 2 being [2-(1-cyclopentenyl)-4-oxo-4H-[1]-beonzopyran-8-yl]acetic acid, or a pharmaceutically acceptable salt, ester or amide thereof.

5. A pharmaceutical composition having antitumor activity which comprises as an active ingredient an effective amount of a compound of the formula:

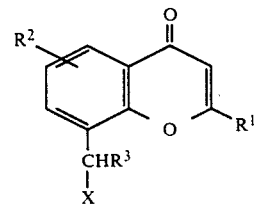

wherein $R^1$ is cycloalkenyl having 3 to 7 carbon atoms; $R^2$ is hydrogen or halogen; $R^3$ is hydrogen or a lower alkyl; and X is carboxyl group, or a pharmaceutically acceptable salt, ester or amide thereof.

* * * * *